US008779186B2

(12) United States Patent
Drysdale et al.

(10) Patent No.: US 8,779,186 B2
(45) Date of Patent: Jul. 15, 2014

(54) PROCESS FOR THE SYNTHESIS OF FLUORINATED ETHERS OF AROMATIC ACIDS

(75) Inventors: Neville Everton Drysdale, Newark, DE (US); Kenneth Gene Moloy, Hockessin, DE (US); Joachim C. Ritter, Wilmington, DE (US); Joel M. Pollino, Elkton, MD (US); Surbhi Mahajan Du, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 148 days.

(21) Appl. No.: 12/874,452

(22) Filed: Sep. 2, 2010

(65) Prior Publication Data

US 2011/0060116 A1   Mar. 10, 2011

Related U.S. Application Data

(60) Provisional application No. 61/239,107, filed on Sep. 2, 2009.

(51) Int. Cl.
*C07C 65/00* (2006.01)
*C07C 69/82* (2006.01)
*C07C 69/80* (2006.01)
*C07C 65/24* (2006.01)

(52) U.S. Cl.
CPC ............. *C07C 69/80* (2013.01); *C07C 69/82* (2013.01); *C07C 65/24* (2013.01)
USPC ........... 562/473; 562/465; 562/471; 562/474; 528/206

(58) Field of Classification Search
None
See application file for complete search history.

(56) References Cited

U.S. PATENT DOCUMENTS

| 3,047,536 | A |   | 7/1962 | Gordon |
| 3,227,680 | A |   | 1/1966 | Tamblyn et al. |
| 3,554,966 | A |   | 1/1971 | Jones et al. |
| 4,292,402 | A | * | 9/1981 | Pollet et al. ............. 430/631 |
| 4,737,571 | A |   | 4/1988 | Hodge et al. |
| 5,674,969 | A |   | 10/1997 | Sikkema et al. |
| 5,693,227 | A |   | 12/1997 | Costa |
| 6,288,271 | B1 | * | 9/2001 | Gutman et al. ............. 562/493 |
| 6,849,762 | B2 | * | 2/2005 | Fabian et al. ............. 562/474 |

FOREIGN PATENT DOCUMENTS

| CA | 2355316 | 4/2001 |
| WO | 2006/104974 | 10/2006 |
| WO | 2008-082510 A1 | 7/2008 |

OTHER PUBLICATIONS

Huo et al, Jiangxi Shifan Daxue Xuebao, Ziran Kexueban, 2006, 30(6), 524-527.*
Pospiech et al, Polymer Preprints (American Chemical Society, Division of Polymer Chemistry) (1998), 39(2), 882-883.*
Alpermann et al, Archiv der Pharmazie (Weinheim, Germany), 1979, 312(2), 94-100.*
Neville Everton Drysdale, U.S. Appl. No. 12/873,423, filed Sep. 1, 2010.
Neville Everton Drysdale, U.S. Appl. No. 12/873,428, filed Sep. 1, 2010.
Neville Everton Drysdale, U.S. Appl. No. 12/873,392, filed Sep. 1, 2010.
Neville Everton Drysdale, U.S. Appl. No. 12/873,396, filed Sep. 1, 2010.
Neville Everton Drysdale, U.S. Appl. No. 12/873,402, filed Sep. 1, 2010.
Neville Everton Drysdale, U.S. Appl. No. 12/873,418, filed Sep. 1, 2010.
Joachim C. Ritter, U.S. Appl. No. 12/874,525, filed Sep. 2, 2010.
Joachim C. Ritter, U.S. Appl. No. 12/874,497, filed Sep. 2, 2010.
Joachim C. Ritter, U.S. Appl. No. 12/874,474, filed Sep. 2, 2010.
Joachim C. Ritter, U.S. Appl. No. 12/874,430, filed Sep. 2, 2010.
International Search Report, International Application No. PCT/US2010/047595, Dated Mar. 25, 2011.
Jenichen D. et al., "Self Organization in Semifluorinated Polymers", Materials Science Forum, 2004, vols. 443-444, pp. 223-226.

* cited by examiner

*Primary Examiner* — Sudhakar Katakam

(57) ABSTRACT

New fluorinated ethers of aromatic acids and diesters are disclosed. These compositions can be applied to, e.g., fibers, yarns, carpets, garments, films, molded parts, paper and cardboard, stone, and tile to impart soil, water and oil resistance. By incorporating the fluorinated ethers of aromatic acids, or diesters thereof, into polymer backbones, more lasting soil, water and oil resistance, as well as improved flame retardance, can be achieved.

9 Claims, No Drawings

PROCESS FOR THE SYNTHESIS OF FLUORINATED ETHERS OF AROMATIC ACIDS

This application claims priority under 35 U.S.C. §119(e) from, and claims the benefit of, U.S. Provisional Application No. 61/239,107, filed Sep. 2, 2009, which is by this reference incorporated in its entirety as a part hereof for all purposes.

TECHNICAL FIELD

This invention relates to the manufacture of fluorinated ethers of aromatic acids or hydroxy aromatic acids, which are valuable for a variety of purposes such as use as surfactants, intermediates or as monomers to make polymers.

BACKGROUND

Fluorinated organic compounds have been used in a wide variety of applications, for example, in surface treatments, as intermediates in the synthesis of compounds such as pharmaceuticals, and as monomers in the synthesis of polymers with highly valued properties. In particular, as compounds or as components of polymers, they are used to impart soil, water and oil resistance, and improved flame retardancy to materials, especially in fiber-related industries. Generally, the fluorinated compounds are applied as a topical treatment, but their effectiveness decreases over time because of material loss resulting from wear and washing.

A need thus remains to provide polymeric materials that have improved, more durable soil and oil resistance.

SUMMARY

Provided herein are new compositions or compounds as represented by the structure of the following Formula I:

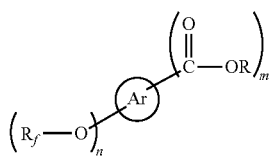

wherein:
Ar is a $C_6$~$C_{20}$ monocyclic or polycyclic aromatic nucleus,
n and m are each independently a nonzero value,
n+m is less than or equal to 8,
$R_f$ is a fluorinated alkyl, alkaryl, aralkyl, or aryl group, optionally containing one or more ether linkages —O—; and
R is H or a branched or linear $C_{1\ to\ 10}$ alkyl group.

Another embodiment of this invention provides a process for preparing a compound, monomer, oligomer or polymer by preparing a fluorinated ether of an aromatic acid as is represented by the structure of Formula I, and then subjecting the ether so produced to a reaction (including a multi-step reaction) to prepare therefrom a compound, monomer, oligomer or polymer.

It has been found that by incorporating fluorinated aromatic diesters into polymer backbones, more lasting soil, water and oil resistance, as well as improved flame retardance, can be achieved in fiber-related products made therefrom.

DETAILED DESCRIPTION

This disclosure provides new compositions or compounds as represented by the structure of the following Formula I:

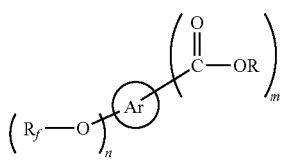

wherein:
Ar is a $C_6$~$C_{20}$ monocyclic or polycyclic aromatic nucleus,
n and m are each independently a nonzero value,
n+m is less than or equal to 8,
$R_f$ is a fluorinated alkyl, alkaryl, aralkyl, or aryl group, optionally containing one or more ether linkages —O—; and
R is H or a branched or linear $C_{1\ to\ 10}$ alkyl group.

Examples of $R_f$ groups as used in the above Formula I include without limitation:
$CF_3(CF_2)_a(CH_2)_b$— wherein a=an integer from 0 to 15 and b=1, 3 or 4;
$HCF_2(CF_2)_c(CH_2)_d$— wherein c=an integer from 0 to 15 and d=1, 3, or 4;
$CF_3CF_2CF_2OCFHCF_2(OCH_2CH_2)_e$— and
$CF_3CF_2CF_2OCF_2CF_2(OCH_2CH_2)_e$—, wherein e=an integer from 1 to 12;
$(CF_3)_2CH$—,
$(CF_3CF_2CFH)(F)(CF_3)C$—,
$(CF_3CF_2CFH)(F)(CF_3)CCH_2$—,
$(CF_3)_2(H)C(CF_3CF_2)(F)C$—,
$(CF_3)_2(H)C(CF_3CF_2)(F)CCH_2$—,
pentafluorophenyl,
$CF_3(CF_2)_f(CH_2)_2$— wherein f=an integer from 0 to 15,
$HCF_2(CF_2)_g(CH_2)_h$— wherein g=an integer from 0 to about 15 and h=0 or 2,
$CF_3CF_2CF_2OCFHCF_2$—,
$CF_3CF_2CF_2OCF_2CF_2$—,
$CF_3CF_2(CH_2CH_2CF_2CF_2)_iCH_2CH_2$—,
$CF_3CF_2CF_2CF_2(CH_2CH_2CF_2CF_2)_iCH_2CH_2$—,
$CF_3CF_2(CH_2CF_2)_iCH_2CH_2$—,
$CF_3CF_2CF_2CF_2(CH_2CF_2)_iCH_2CH_2$—, wherein i=an integer from 1 to 6; and
$CF_3CFHCF_2$—.

As used herein, the term "alkyl" denotes a univalent group derived from an alkane by removing a hydrogen atom from any carbon atom: —$C_xH_{2x+1}$ where x≥1.

As used herein, the term "aryl" denotes a univalent group whose free valence is to a carbon atom of an aromatic ring.

As used herein, the term "aralkyl" denotes an alkyl group which bears an aryl group. One such example is the benzyl group, i.e. the radical,

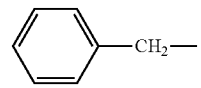

As used herein, the term "alkaryl" denotes an aryl group which bears an alkyl group. Some examples are the 4-methylphenyl radical,

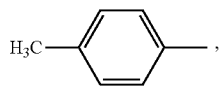

the mesityl group (i.e. 2,4,6-trimethylphenyl) and the 2,6-diisopropylphenyl group (i.e., the $(CH_3CHCH_3)_2C_6H_3$-radical).

The radical denoted by

is an n+m valent $C_6$–$C_{20}$ monocyclic or polycyclic aromatic nucleus formed by the removal of n+m hydrogens from different carbon atoms on the aromatic ring, or on the aromatic rings when the structure is polycyclic. The radical "Ar" may be substituted or unsubstituted; when unsubstituted, it contains only carbon and hydrogen.

One example of a suitable Ar group is phenylene, as shown below, wherein n=m=1.

A preferred Ar group is shown below, wherein n=m=2.

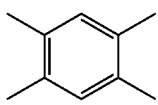

In one embodiment of this invention, new compositions or compounds as represented by the structure of the following Formula II

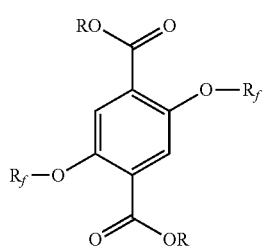

are provided. In this compound, Ar is

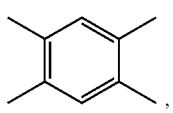

n=m=2.

In another embodiment of this invention, new compositions or compounds as represented by the structure of the following Formula III

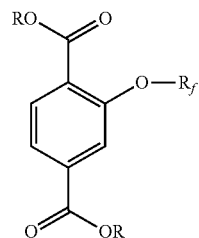

are provided. In this compound, Ar is

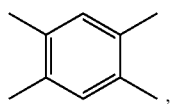

n=1, and m=2.

When R is H and $R_f$ is not attached to the ether oxygen in Formula I via a $CF_2$ group or a $CF_2CH_2CH_2$ group, compositions of Formula I can be made by the following copper-catalyzed process:

(a) contacting a halogenated aromatic acid that is described by the structure of Formula IV

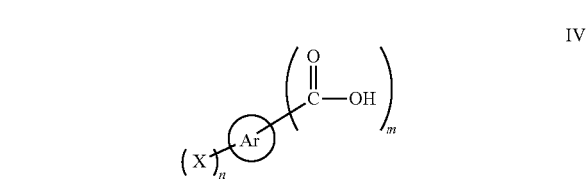

wherein each X is independently Cl, Br, or I, and Ar, n and m are as set forth above, with
(i) a total of from about n+m to about n+m+1 equivalents of the alcoholate $RfO^-M^+$ (wherein M is Na or K) per equivalent of halogenated aromatic acid, in a polar aprotic solvent or in RfOH as a solvent;
(ii) a copper (I) or copper (II) source; and
(iii) a ligand that coordinates to copper, wherein said ligand is a diamine, diketones, Schiff Base, or amino acid,
to form a reaction mixture;
(b) heating the reaction mixture to form the m-basic salt of the product of step (a), as described by the structure of Formula V;

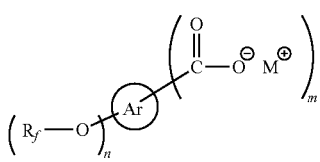

(c) optionally, separating the Formula V m-basic salt from the reaction mixture in which it is formed; and
(d) contacting the Formula V m-basic salt with acid to form therefrom a fluorinated ether of an aromatic acid.

An "m-basic salt", as the term is used herein, is the salt formed from an acid that contains in each molecule m acid groups having a replaceable hydrogen atom.

Examples of $R_f$ groups that are not attached to the ether oxygen in Formula I via a $CF_2$ group or a $CF_2CH_2CH_2$ group include without limitation:

$CF_3(CF_2)_a(CH_2)_b$— wherein a=an integer from 0 to 15 and b=1, 3 or 4;

$HCF_2(CF_2)_c(CH_2)_d$— wherein c=an integer from 0 to 15 and d=1, 3, or 4;

$CF_3CF_2CF_2OCFHCF_2(OCH_2CH_2)_e$— and $CF_3CF_2CF_2OCF_2CF_2(OCH_2CH_2)_e$—, wherein e=an integer from 1 to 12;

$(CF_3)_2CH$—, $(CF_3CF_2CFH)(F)(CF_3)C$—, $(CF_3CF_2CFH)(F)(CF_3)CCH_2$—, $(CF_3)_2(H)C(CF_3CF_2)(F)C$—, $(CF_3)_2(H)C(CF_3CF_2)(F)CCH_2$—; and pentafluorophenyl.

Various halogenated aromatic acids, to be used as a starting material in a copper-cartalyzed process to make compositions of Formula I wherein R═H and $R_f$ is not attached to the ether oxygen via a $CF_2$ group or a $CF_2CH_2CH_2$ group, are commercially available. For example, 2-bromobenzoic acid is available from Aldrich Chemical Company (Milwaukee, Wis.). It can be synthesized, however, by oxidation of bromomethylbenzene as described in Sasson et al, *Journal of Organic Chemistry* (1986), 51(15), 2880-2883. Other halogenated aromatic acids that can be used include without limitation 2,5-dibromobenzoic acid, 2-bromo-5-nitrobenzoic acid, 2-bromo-5-methylbenzoic acid, 2-chlorobenzoic acid, 2,5-dichlorobenzoic acid, 2-chloro-3,5-dinitrobenzoic acid, 2-chloro-5-methylbenzoic acid, 2-bromo-5-methoxybenzoic acid, 5-bromo-2-chlorobenzoic acid, 2,3-dichlorobenzoic acid, 2-chloro-4-nitrobenzoic acid, 2,5-dichloroterephthalic acid, 2-chloro-5-nitrobenzoic acid, 2,5-dibromoterephthalic acid, and 2,5-dichloroterephthalic acid, all of which are commercially available. Preferably, the halogenated aromatic acid is 2,5-dibromoterephthalic acid or 2,5-dichloroterephthalic acid.

Other halogenated aromatic acids useful as a starting material in a copper catalyzed process include those shown in the left column of the table below, wherein X═Cl, Br or I, and wherein the corresponding ether of an aromatic acid produced therefrom by the process of this invention is shown in the right column:

| $(COOH)_m$—Ar—$(X)_n$ | $(COOH)_m$—Ar—$(OR_f)_n$ |
|---|---|
| 1-X, 2-COOH naphthalene | 1-$OR_f$, 2-COOH naphthalene |
| 1-COOH, 4-X naphthalene | 1-COOH, 4-$OR_f$ naphthalene |
| 1-X, 2-COOH, 5-X, 6-COOH naphthalene | 1-$OR_f$, 2-COOH, 5-$OR_f$, 6-COOH naphthalene |
| 1-COOH, 3-X, 6-X naphthalene (5-COOH) | 1-COOH, 3-$OR_f$, 6-$OR_f$ naphthalene (5-COOH) |
| 1,2-di-X, 2,3-di-COOH benzene | 1,2-di-$OR_f$, 2,3-di-COOH benzene |
| 1,3-di-COOH, 2-X, 5-COOH benzene | 1,3-di-COOH, 2-$OR_f$, 5-COOH benzene |
| tetra-COOH, di-X benzene | tetra-COOH, di-$OR_f$ benzene |
| biphenyl-2-COOH, 3'-X | biphenyl-2-COOH, 3'-$OR_f$ |
| biphenyl-2,2'-di-COOH, 3,3'-di-OH | biphenyl-2,2'-di-COOH, 3,3'-di-$OR_f$ |

The copper source is a Cu(I) salt, a Cu(II) salt, or mixtures thereof. Examples include without limitation CuCl, CuBr, CuI, $Cu_2SO_4$, $CuNO_3$, $CuCl_2$, $CuBr_2$, $CuI_2$, $CuSO_4$, and $Cu(NO_3)_2$. The selection of the copper source may be made in relation to the identity of the halogenated aromatic acid used. For example, if the starting halogenated aromatic acid is a bromobenzoic acid, CuCl, CuBr, CuI, $Cu_2SO_4$, $CuNO_3$, $CuCl_2$, $CuBr_2$, $CuI_2$, $CuSO_4$, and $Cu(NO_3)_2$ will be included among the useful choices. If the starting halogenated aromatic acid is a chlorobenzoic acid, CuBr, CuI, $CuBr_2$ and $CuI_2$ will be included among the useful choices.

The copper-catalyzed processes for making a compound hereof are described in greater detail in copending U.S. Provisional Patent Applications 61/239,102, 61/239,103, 61/239,106, and 61/239,194, each of which is by this reference incorporated in its entirety as a part hereof for all purposes.

Compositions described by Formula I wherein (1) R is not H, or (2) R is H and $R_f$ is attached to the ether oxygen in Formula I via a $CF_2$ group or a $CF_2CH_2CH_2$ group, can be made using synthetic routes other than the copper-catalyzed processes described above. Examples of such $R_f$ groups include without limitation:

$CF_3(CF_2)_f(CH_2)_2$— wherein f=an integer from 0 to 15, $HCF_2(CF_2)_g(CH_2)_h$— wherein g=an integer from 0 to about 15 and h=0 or 2, $CF_3CF_2CF_2OCFHCF_2$—, $CF_3CF_2CF_2OCF_2CF_2$—, $CF_3CF_2(CH_2CH_2CF_2CF_2)_iCH_2CH_2$—, $CF_3CF_2CF_2CF_2(CH_2CH_2CF_2CF_2)_iCH_2CH_2$—, $CF_3CF_2(CH_2CF_2)_iCH_2CH_2$—, $CF_3CF_2CF_2CF_2(CH_2CF_2)_iCH_2CH_2$—, wherein i=an integer from 1 to 6; and $CF_3CFHCF_2$—.

Such compositions can be prepared, for example, by the addition of a phenol to a fluorinated olefin. Such reactions are described, for example, in Feiring and Wonchoba, *Journal of Organic Chemistry* (1992), 57(26), 7014-17; U.S. Pat. No. 5,198,570; U.S. Patent Publication No. 2005/065382; and Furin et al, *Journal of Fluorine Chemistry* (2000), 106(1), 13-24. For example, in order to prepare a composition described by Formula III wherein Rf is $CF_2HCF_2$—, one would react the appropriate phenol with tetrafluoroethylene in the presence of base in a polar solvent or solvent mixture:

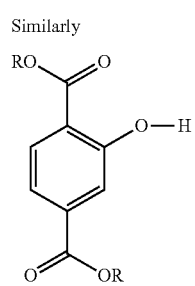

Similarly

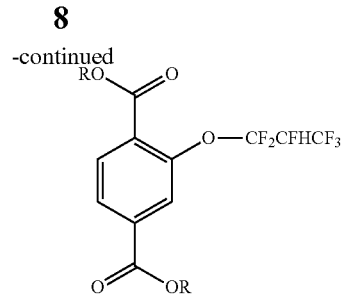

Alternatively, the compositions can be made by the coupling of alcohols and phenols to form aryl ethers using triphenylphosphine and diethyl azodicarboxylate ("DEAD"). One scheme is shown below (Example 3):

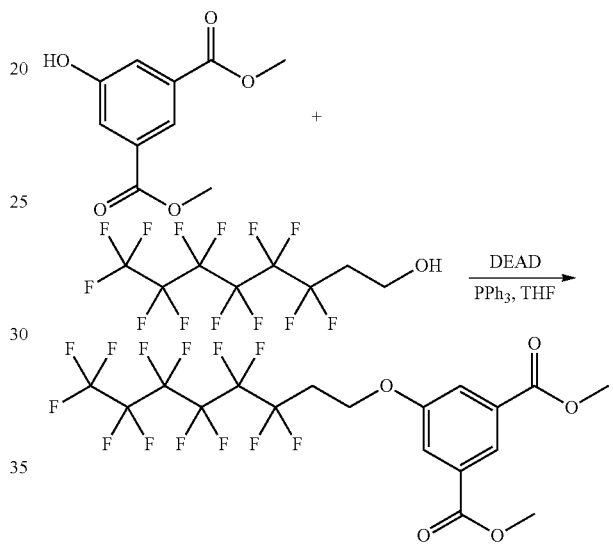

This is a version of the Mitsunobu Reaction, as described for example in Mundy, Bradford P. et al, *Name Reactions and Reagents in Organic Synthesis,* 2nd Edition, John Wiley & Sons, Hoboken, N.J. (2005). The Mitsunobu Reaction was applied to the preparation of fluorinated aryl ethers by A. V. Malkov et al [*Journal of Organic Chemistry* (2007), 72(4), 1315-1325].

The compositions or compounds of the above Formula I can be applied, for example, to fibers, yarns, carpets, garments, films, molded parts, paper and cardboard, stone, and tile to impart soil, water and oil resistance thereto. By incorporating the fluorinated ethers of aromatic acids, or diesters thereof, into polymer backbones, however, more lasting soil, water and oil resistance, as well as improved flame retardance, can be achieved.

Compositions or compounds of Formula I as prepared herein can thus be used in turn in the synthesis of products such as a compound, a monomer, or an oligomer or polymer thereof. These produced materials may have one or more of ester functionality, ether functionality, amide functionality, imide functionality, imidazole functionality, thiazole functionality, oxazole functionality, carbonate functionality, acrylate functionality, epoxide functionality, urethane functionality, acetal functionality, or anhydride functionality.

A Formula I compound may, as desired, be isolated and recovered as described above. It may also be subjected with or without recovery from the reaction mixture to further steps to convert it to another product such as another compound (e.g.

a monomer), or an oligomer or a polymer. Another embodiment of a process hereof thus provides a process for converting a Formula I compound, through one or more reactions, into another compound, or into an oligomer or a polymer. A Formula I compound may be made by a process such as described above, and then may be subjected, for example, to a polymerization reaction to prepare an oligomer or polymer therefrom, such as those having ester functionality or amide functionality, or a pyridobisimidazole-2,6-diyl(2,5-dihydroxy-p-phenylene) polymer.

The compounds of Formula I made by the process disclosed herein, in particular the dimethyl esters, can be used in condensation polymerizations to produce fluorinated condensation polymers, e.g. those including without limitation polyesters, polyamides, polyimides, and polybenzimidazoles. Representative reactions involving a material of this invention, or a derivative of such material, such as a diester, include, for example, making a polyester from one or more compounds of Formula I and either diethylene glycol or triethylene glycol in the presence of 0.1% of $Zn_3(BO_3)_2$ in 1-methylnaphthalene under nitrogen, according to the method taught in U.S. Pat. No. 3,047,536 (which is incorporated in its entirety as a part hereof for all purposes). Similarly, a fluorinated ether of aromatic acid is suitable for copolymerization with a dibasic acid and a glycol to prepare a heat-stabilized fluorinated polyester according to the method taught in U.S. Pat. No. 3,227,680 (which is incorporated in its entirety as a part hereof for all purposes), wherein representative conditions involve forming a prepolymer in the presence of titanium tetraisopropoxide in butanol at 200–250° C., followed by solid-phase polymerization at 280° C. at a pressure of 0.08 mm Hg.

Other diols useful to make a polyester from a Formula I compound are those that are derived from a fermentation process, and another embodiment of this invention thus involves a process for making from a Formula I compound an oligomer or polymer that further includes a step of providing a diol to such a process from a fermentation process.

A Formula I compound may be converted into a polyamide oligomer or polymer by reaction with a diamine in a process in which, for example, the polymerization takes place in solution in an organic compound that is liquid under the conditions of the reaction, is a solvent for both the Formula I compound and the diamine, and has a swelling or partial salvation action on the polymeric product. The reaction may be effected at moderate temperatures, e.g. under 100° C., and is preferably effected in the presence of an acid acceptor that is also soluble in the chosen solvent. Suitable solvents include methyl ethyl ketone, acetonitrile, N,N-dimethylacetamide dimethyl formamide containing 5% lithium chloride, and N-methylpyrrolidone containing a quaternary ammonium chloride such as methyl tri-n-butyl ammonium chloride or methyl-tri-n-propyl ammonium chloride. Combination of the reactant components causes generation of considerable heat and the agitation, also, results in generation of heat energy. For that reason, the solvent system and other materials are cooled at all times during the process when cooling is necessary to maintain the desired temperature. Processes similar to the foregoing are described in U.S. Pat. No. 3,554,966; U.S. Pat. No. 4,737,571; and CA 2,355,316.

A Formula I compound may also be converted into a polyamide oligomer or polymer by reaction with a diamine in a process in which, for example, a solution of the diamine in a solvent may be contacted in the presence of an acid acceptor with a solution of the Formula I compound in a second solvent that is immiscible with the first to effect polymerization at the interface of the two phases. The diamine may, for example, be dissolved or dispersed in a water containing base with the base being used in sufficient quantities to neutralize the acid generated during polymerization. Sodium hydroxide may be used as the acid acceptor. Preferred solvents for the diacid (halide) are tetrachloroethylene, methylenechloride, naphtha and chloroform. The solvent for the Formula I compound should be a relative non-solvent for the amide reaction product, and be relatively immiscible in the amine solvent. A preferred threshold of immiscibility is as follows: an organic solvent should be soluble in the amine solvent not more than between 0.01 weight percent and 1.0 weight percent. The diamine, base and water are added together and vigorously stirred. High shearing action of the stirrer is important. The solution of acid chloride is added to the aqueous slurry. Contacting is generally carried out at from 0° C. to 60° C., for example, for from about 1 second to 10 minutes, and preferably from 5 seconds to 5 minutes at room temperature. Polymerization occurs rapidly. Processes similar to the foregoing are described in U.S. Pat. No. 3,554,966 and U.S. Pat. No. 5,693,227.

A fluorinated ether of aromatic acid can also be polymerized with the trihydrochloride-monohydrate of tetraminopyridine in a condensation polymerization in strong polyphosphoric acid under slow heating above 100° C. up to about 180° C. under reduced pressure, followed by precipitation in water, as disclosed in U.S. Pat. No. 5,674,969 (which is incorporated in its entirety as a part hereof for all purposes); or by mixing the monomers at a temperature from about 50° C. to about 110° C., and then 145° C. to form an oligomer, and then reacting the oligomer at a temperature of about 160° C. to about 250° C. as disclosed in U.S. Provisional Application No. 60/665,737, filed Mar. 28, 2005 (which is incorporated in its entirety as a part hereof for all purposes), published as WO 2006/104974. The polymer that may be so produced may be a pyridobisimidazole-2,6-diyl(2,5-dialkoxy-p-phenylene) polymer or a pyridobisimidazole-2,6-diyl(2,5-diareneoxy-p-phenylene) polymer such as a poly(1,4-(2,5-diareneoxy)phenylene-2,6-pyrido[2,3-d: 5,6-d']bisimidazole) polymer. The pyridobisimidazole portion thereof may, however, be replaced by any one or more of a benzobisimidazole, benzobisthiazole, benzobisoxazole, pyridobisthiazole and a pyridobisoxazole; and the 2,5-dialkoxy-p-phenylene portion thereof may be replaced by an alkyl or aryl ether of one or more of isophthalic acid, terephthalic acid, 2,5-pyridine dicarboxylic acid, 2,6-naphthalene dicarboxylic acid, 4,4'-diphenyl dicarboxylic acid, 2,6-quinoline dicarboxylic acid, and 2,6-bis(4-carboxyphenyl)pyridobisimidazole, wherein such a fluorinated ether is produced according to the methods disclosed herein.

The polymer prepared in such manner may, for example, contain one or more of the following units:
pyridobisimidazole-2,6-diyl(2,5-dialkoxy-p-phenylene) and/or pyridobisimidazole-2,6-diyl(2,5-diphenoxy-p-phenylene) units;
units selected from the group consisting of pyridobisimidazole-2,6-diyl(2,5-dimethoxy-p-phenylene), pyridobisimidazole-2,6-diyl(2,5-diethoxy-p-phenylene), pyridobisimidazole-2,6-diyl(2,5-dipropoxy-p-phenylene), pyridobisimidazole-2,6-diyl(2,5-dibutoxy-p-phenylene) and pyridobisimidazole-2,6-diyl(2,5-diphenoxy-p-phenylene);
pyridobisthiazole-2,6-diyl(2,5-dialkoxy-p-phenylene) and/or pyridobisthiazole-2,6-diyl(2,5-diphenoxy-p-phenylene) units;
units selected from the group consisting of pyridobisthiazole-2,6-diyl(2,5-dimethoxy-p-phenylene), pyridobisthiazole-2,6-diyl(2,5-diethoxy-p-phenylene), pyridobisthiazole-2,6-diyl(2,5-dipropoxy-p-phenylene), pyridobisthiazole-2, 6-diyl(2,5-dibutoxy-p-phenylene) and pyridobisthiazole-2, 6-diyl(2,5-diphenoxy-p-phenylene); pyridobisoxazole-2,6-diyl(2,5-dialkoxy-p-phenylene) and/or pyridobisoxazole-2, 6-diyl(2,5-diphenoxy-p-phenylene) units;

units selected from the group consisting of pyridobisoxazole-2,6-diyl(2,5-dimethoxy-p-phenylene), pyridobisoxazole-2,6-diyl(2,5-diethoxy-p-phenylene), pyridobisoxazole-2,6-diyl(2,5-dipropoxy-p-phenylene), pyridobisoxazole-2,6-diyl(2,5-dibutoxy-p-phenylene) and pyridobisoxazole-2,6-diyl(2,5-diphenoxy-p-phenylene);

benzobisimidazole-2,6-diyl(2,5-dialkoxy-p-phenylene) and/or benzobisimidazole-2,6-diyl(2,5-diphenoxy-p-phenylene) units;

units selected from the group consisting of benzobisimidazole-2,6-diyl(2,5-dimethoxy-p-phenylene), benzobisimidazole-2,6-diyl(2,5-diethoxy-p-phenylene), benzobisimidazole-2,6-diyl(2,5-dipropoxy-p-phenylene), benzobisimidazole-2,6-diyl(2,5-dibutoxy-p-phenylene) and benzobisimidazole-2,6-diyl(2,5-diphenoxy-p-phenylene);

benzobisthiazole-2,6-diyl(2,5-dialkoxy-p-phenylene) and/or benzobisthiazole-2,6-diyl(2,5-diphenoxy-p-phenylene) units;

units selected from the group consisting of benzobisthiazole-2,6-diyl(2,5-dimethoxy-p-phenylene), benzobisthiazole-2,6-diyl(2,5-diethoxy-p-phenylene), benzobisthiazole-2,6-diyl(2,5-dipropoxy-p-phenylene), benzobisthiazole-2,6-diyl(2,5-dibutoxy-p-phenylene) and benzobisthiazole-2,6-diyl(2,5-diphenoxy-p-phenylene);

benzobisoxazole-2,6-diyl(2,5-dialkoxy-p-phenylene) and/or benzobisoxazole-2,6-diyl(2,5-diphenoxy-p-phenylene) units; and/or units selected from the group consisting of benzobisoxazole-2,6-diyl(2,5-dimethoxy-p-phenylene), benzobisoxazole-2,6-diyl(2,5-diethoxy-p-phenylene), benzobisoxazole-2,6-diyl(2,5-dipropoxy-p-phenylene), benzobisoxazole-2,6-diyl(2,5-dibutoxy-p-phenylene) and benzobisoxazole-2,6-diyl(2,5-diphenoxy-p-phenylene).

EXAMPLES

The advantageous attributes and effects of the processes hereof may be seen in laboratory examples, as described below. The embodiments of these processes on which the example is based are representative only, and the selection of those embodiments to illustrate the invention does not indicate that conditions, arrangements, approaches, steps, techniques, configurations or reactants not described in the example are not suitable for practicing these processes, or that subject matter not described in the example is excluded from the scope of the appended claims and equivalents thereof.
Materials.

All reagents were used as received. 1,2-bis(methylamino) cyclohexane (97% purity), sodium hydride (95% purity). 2,2, 2-Trifluoroethanol (99% purity), triphenylphosphine (99% purity), and diethyl diazodicarboxylate, (97+% purity) were obtained from Sigma-Aldrich (Milwaukee, Wis., USA). 2,5-dibromoterephthalic acid (98+% purity) was prepared according to the procedure in described in WO 2008/082501. Copper(II) bromide ("$CuBr_2$"), dimethyl 5-hydroxyisophthalate (98% purity), and 1H,1H,2H,2H-perfluorooctanol (97% purity) were obtained from Alfa Aesar (Ward Hill, Mass., USA). was obtained from (Milwaukee, Wis., USA). 2,2,3,3-Tetrafluoropropanol was of 99% purity.

The meaning of abbreviations is as follows: "DEAD" means diethyl azodicarboxylate, "eq" means equivalent(s), "g" means gram(s), "GC" means gas chromatography, "mL" means milliliter(s), "mmol" means millimole(s), "N" means normal, and "NMR" means nuclear magnetic resonance spectroscopy, "$PPh_3$" means triphenyl phosphine, and "THF" means tetrahydrofuran.

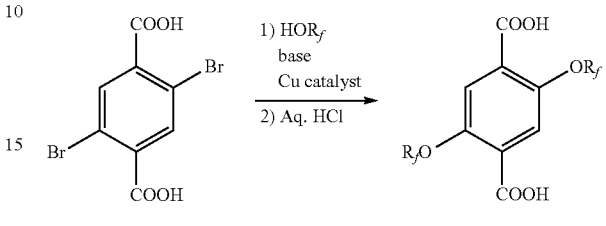

Example 1: $HOR_f = HOCH_2CF_3$
Example 2: $HOR_f = HOCH_2CF_2CF_2H$

Example 1

Preparation of
2,5-bis(2,2,2-trifluoroethoxy)terephthalic acid

To a solution of 8 mL 2,2,2-trifluoroethanol ($CF_3CH_2OH$) in 15 mL of THF was carefully added 0.19 g (7.9 mmol) of sodium hydride. When gas evolution was complete, 0.488 g (1.5 mmol) of 2,5-dibromoterephthalic acid was added to the solution, followed by addition of a solution of $CuBr_2$ (0.092 mmol) and 1,2-bis(methylamino)cyclohexane (0.19 mmol) in 1.5 mL of $CF_3CH_2OH$. The resulting pale blue slurry was heated at 60° C. for four days. Aqueous HCl (1 N) was added to precipitate the product. The product was washed with water, then dissolved in methanol, and the resulting solution was filtered. The methanol was removed under vacuum to give the product as colorless microcrystals. Yield: 0.384 g, 71%.

Elemental analysis: Calculated for $C_{12}H_8F_6O_6$: C, 39.80%; H, 2.23%. Found: C, 39.93%, 2.31%.

NMR analysis: $^1H$ ($CD_3OD$): 7.53 (s, 2H), 4.57 (q, 8.5 Hz, 4H)

$^{13}C$ ($CD_3OD$): 167.7, 152.9, 128.2, 124.9 (q, 277 Hz), 120.4, 69.1 (q, 35.4 Hz).

Example 2

Preparation of
2,5-bis(2,2,3,3-tetrafluoropropoxy)terephthalic acid

A flask was charged with 5 mL of anhydrous THF and 8.1 mmol of sodium hydride. A solution of 1.5 g (11.4 mmol) of 2,2,3,3-tetrafluoropropanol ($HCF_2CF_2CH_2OH$) in 5 mL of THF was added dropwise. When gas evolution was complete, 2,5-dibromoterephthalic acid (1.51 mmol) was added to the colorless solution. Next, a mixture of $CuBr_2$ (0.13 mmol) and 1,2-bis(methylamino)cyclohexane (0.22 mmol) in 0.5 g of $HCF_2CF_2CH_2OH$ was added to the solution. The resulting pale blue slurry was heated at 60° C. for two days. The product was isolated by treating the cooled reaction product with 0.5 N HCl, then with water, and washing the precipitate with water. Yield: 0.465 g, 72%.

NMR analysis: $^1$H (CD$_3$OD): 7.56 (s, 2H), 6.39 (tt, 52.8 and 5.7 Hz, 2H), 4.52 (tt, 12.0 and 1.3 Hz, 4H).

Example 3

Preparation of dimethyl 5-(3,3,4,4,5,5,6,6,7,7,8,8,8-tridecafluorooctyloxy)isophthalate

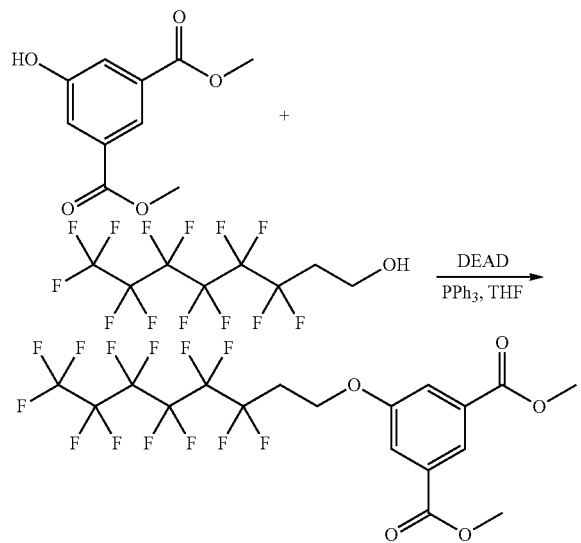

To a 3 neck 100 mL round bottom flask fitted with a stir bar, addition funnel, and a thermocouple, under nitrogen, was added dimethyl 5-hydroxyisophthalate (1.0 g, 0.0048 mol, 1.0 eq) and dry tetrahydrofuran (25 mL). The reaction was cooled to −5° C., followed by the addition of triphenylphosphine (1.5 g, 0.0057 mol, 1.2 eq), 1H,1H,2H,2H-perfluorooctanol (2.1 g, 0.0057 mol, 1.2 eq), then by the dropwise addition of a solution of diethyl azodicarboxylate (DEAD) (1.0 g, 0.0057 mol, 1.2 eq) in 5 mL of dry tetrahydrofuran. The DEAD addition was slightly exothermic (−5° C. to 5° C.). The cold bath was removed and the reaction was stirred overnight at ambient temperature.

After approximately 16 hours, GC analysis showed partial conversion of the dimethyl 5-hydroxyisophthalate (22%) and formation of the desired product. Unreacted PPh$_3$ and 1H,1H,2H,2H-perfluorooctanol were also observed. The product was isolated by flash column chromatography (silica gel 60, dichloromethane-hexanes) as a colorless oil in 35% yield based on unreacted dimethyl 5-hydroxyisophthalate NMR (CDCl$_3$): $^1$H, 8.32 (s, 1H), 2.05 (s, 2H), 4.36 (m, 2H), 3.95 (s, 6H), 2.67 (m, 2H). $^{13}$C (carbons with direct fluorine attachment omitted): 166.0 (s), 158.3 (s), 132.1 (s), 123.8 (s), 119.8 (s), 60.7 (s), 52.5 (s), 31.3 (t, J$_{CF}$=22 Hz). MS: M$^+$ (556 amu), M-OCH$_3$$^+$ (525 amu), M-CO$_2$CH$_3$$^+$ (497 amu).

In this specification, each of the formulae shown herein describes each and all of the separate, individual compounds that can be formed in that formula by (1) selection from within the prescribed range for one of the variable radicals, substituents or numerical coefficients while all of the other variable radicals, substituents or numerical coefficients are held constant, and (2) performing in turn the same selection from within the prescribed range for each of the other variable radicals, substituents or numerical coefficients with the others being held constant. In addition to a selection made within the prescribed range for any of the variable radicals, substituents or numerical coefficients of only one of the members of the group described by the range, a plurality of compounds may be described by selecting more than one but less than all of the members of the whole group of radicals, substituents or numerical coefficients. When the selection made within the prescribed range for any of the variable radicals, substituents or numerical coefficients is a subgroup containing (i) only one of the members of the whole group described by the range, or (ii) more than one but less than all of the members of the whole group, the selected member(s) are selected by omitting those member(s) of the whole group that are not selected to form the subgroup. The compound, or plurality of compounds, may in such event be characterized by a definition of one or more of the variable radicals, substituents or numerical coefficients that refers to the whole group of the prescribed range for that variable but where the member(s) omitted to form the subgroup are absent from the whole group.

Where a range of numerical values is recited herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, amounts, sizes, ranges and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

Where an embodiment of this invention is stated or described as comprising, including, containing, having, being composed of or being constituted by certain features, it is to be understood, unless the statement or description explicitly provides to the contrary, that one or more features in addition to those explicitly stated or described may be present in the embodiment. An alternative embodiment of this invention, however, may be stated or described as consisting essentially of certain features, in which embodiment features that would materially alter the principle of operation or the distinguishing characteristics of the embodiment are not present therein. A further alternative embodiment of this invention may be stated or described as consisting of certain features, in which embodiment, or in insubstantial variations thereof, only the features specifically stated or described are present.

What is claimed is:

1. A compound as represented by the structure of the following Formula I:

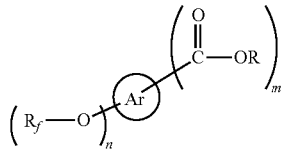

wherein:
Ar is a $C_6$ or $C_{10}$ monocyclic or polycyclic aromatic nucleus,
m=2,
n+m is less than or equal to 8,
$R_f$ is a fluorinated, alkyl group, optionally containing one or more ether linkages —O—, selected from the group consisting of $HCF_2(CF_2)_c(CH_2)_d$— wherein c=an integer from 0 to 15 and d=1, 3, or 4;
$CF_3CF_2CF_2OCFHCF_2(OCH_2CH_2)_e$— and $CF_3CF_2CF_2OCF_2CF_2(OCH_2CH_2)_e$—, wherein e=an integer from 1 to 12;
$(CF_3)_2CH$—,
$(CF_3CF_2CFH)(F)(CF_3)C$—,
$(CF_3CF_2CFH)(F)(CF_3)CCH_2$—,
$(CF_3)_2(H)C(CF_3CF_2)(F)C$—,
$(CF_3)_2(H)C(CF_3CF_2)(F)CCH_2$—,
pentafluorophenyl,
$HCF_2(CF_2)_g(CH_2)_h$— wherein g=an integer from 0 to about 15 and h=0 or 2,
$CF_3CF_2CF_2OCFHCF_2$—,
$CF_3CF_2CF_2OCF_2CF_2$—,
$CF_3CF_2(CH_2CH_2CF_2CF_2)_iCH_2CH_2$—,
$CF_3CF_2CF_2CF_2(CH_2CH_2CF_2CF_2)_iCH_2CH_2$—,
$CF_3CF_2(CH_2CF_2)_iCH_2CH_2$—, and
$CF_3CF_2CF_2CF_2(CH_2CF_2)_iCH_2CH_2$—, wherein i=an integer from 1 to 6; and
R is H or a branched or linear $C_{1\ to\ 10}$ alkyl group.

2. A compound as represented by the structure of the following Formula II:

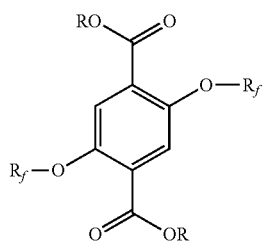

wherein $R_f$ is a fluorinated alkyl group, optionally containing one or more ether linkages —O—; selected from the group consisting of $HCF_2(CF_2)_c(CH_2)_d$— wherein c=an integer from 0 to 15 and d=1, 3, or 4;
$CF_3CF_2CF_2OCFHCF_2(OCH_2CH_2)_e$— and $CF_3CF_2CF_2OCF_2CF_2(OCH_2CH_2)_e$—, wherein e=an integer from 1 to 12;
$(CF_3)_2CH$—,
$(CF_3CF_2CFH)(F)(CF_3)C$—,
$(CF_3CF_2CFH)(F)(CF_3)CCH_2$—,
$(CF_3)_2(H)C(CF_3CF_2)(F)C$—,
$(CF_3)_2(H)C(CF_3CF_2)(F)CCH_2$—,
pentafluorophenyl,
$HCF_2(CF_2)_g(CH_2)_h$— wherein g=an integer from 0 to about 15 and h=0 or 2,
$CF_3CF_2CF_2OCFHCF_2$—,
$CF_3CF_2CF_2OCF_2CF_2$—,
$CF_3CF_2(CH_2CH_2CF_2CF_2)_iCH_2CH_2$—,
$CF_3CF_2CF_2CF_2(CH_2CH_2CF_2CF_2)_iCH_2CH_2$—,
$CF_3CF_2(CH_2CF_2)_iCH_2CH_2$—,
$CF_3CF_2CF_2CF_2(CH_2CF_2)_iCH_2CH_2$—, wherein i=an integer from 1 to 6, and
$CF_3CFHCF_2$—; and
and R is H or a branched or linear $C_{1\ to\ 10}$ alkyl group.

3. A compound as represented by the structure of the following Formula III:

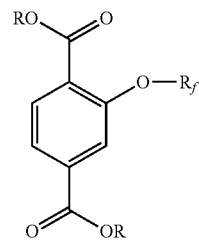

$R_f$ is a fluorinated alkyl group, optionally containing one or more ether linkages —O—, selected from the group consisting of $HCF_2(CF_2)_c(CH_2)_d$— wherein c=an integer from 0 to 15 and d=1, 3, or 4;
$CF_3CF_2CF_2OCFHCF_2(OCH_2CH_2)_e$— and $CF_3CF_2CF_2OCF_2CF_2(OCH_2CH_2)_e$—, wherein e=an integer from 1 to 12;
$(CF_3)_2CH$—,
$(CF_3CF_2CFH)(F)(CF_3)C$—,
$(CF_3CF_2CFH)(F)(CF_3)CCH_2$—,
$(CF_3)_2(H)C(CF_3CF_2)(F)C$—,
$(CF_3)_2(H)C(CF_3CF_2)(F)CCH_2$—,
pentafluorophenyl,
$HCF_2(CF_2)_g(CH_2)_h$— wherein g=an integer from 0 to about 15 and h=0 or 2,
$CF_3CF_2CF_2OCFHCF_2$—,
$CF_3CF_2CF_2OCF_2CF_2$—,
$CF_3CF_2(CH_2CH_2CF_2CF_2)_iCH_2CH_2$—,
$CF_3CF_2CF_2CF_2(CH_2CH_2CF_2CF_2)_iCH_2CH_2$—,
$CF_3CF_2(CH_2CF_2)_iCH_2CH_2$—,
$CF_3CF_2CF_2CF_2(CH_2CF_2)_iCH_2CH_2$—, wherein i=an integer from 1 to 6, and
$CF_3CFHCF_2$—; and R is H or a branched or linear $C_{1\ to\ 10}$ alkyl group.

4. A monomer, oligomer or polymer that comprises a compound according to claim 1.

5. A monomer, oligomer or polymer according to claim 4 that comprises one or more functionalities selected from the group consisting of ester functionality, ether functionality, amide functionality, imide functionality, imidazole functionality, thiazole functionality, oxazole functionality, carbonate functionality, acrylate functionality, epoxide functionality, urethane functionality, acetal functionality, and anhydride functionality.

6. An article of manufacture that comprises a compound according to claim 1.

7. An article of manufacture that comprises a monomer, oligomer or polymer according to claim 5.

8. An article according to claim 6 which is fabricated as fiber, yarn, carpet, a garment, a film, a molded part, paper, cardboard, stone or tile.

9. An article according to claim 7 which is fabricated as fiber, yarn, carpet, a garment, a film, a molded part, paper, cardboard, stone or tile.

* * * * *